United States Patent
Yoshimura et al.

(10) Patent No.: US 6,765,020 B2
(45) Date of Patent: *Jul. 20, 2004

(54) DRUGS FOR PREVENTION AND TREATMENT OF DISEASES CAUSED BY ABNORMALITIES IN CARTILAGE TISSUES

(75) Inventors: Satomichi Yoshimura, Takatsuki (JP); Kengo Akimoto, Osaka (JP); Masashi Matsui, Suita (JP)

(73) Assignee: Suntory Limited, Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,176
(22) PCT Filed: Aug. 7, 1996
(86) PCT No.: PCT/JP96/02231
  § 371 (c)(1),
  (2), (4) Date: Apr. 7, 1997
(87) PCT Pub. No.: WO97/05863
  PCT Pub. Date: Feb. 20, 1997

(65) Prior Publication Data
  US 2002/0012690 A1 Jan. 31, 2002

(30) Foreign Application Priority Data
  Aug. 7, 1995 (JP) .............................. 7-201050

(51) Int. Cl.$^7$ .......................... A61K 31/20; A61K 9/70; A23K 1/165; A23K 1/17
(52) U.S. Cl. ................ 514/558; 424/442; 424/448
(58) Field of Search ............................. 424/442, 443; 514/558

(56) References Cited

U.S. PATENT DOCUMENTS 5,260,336 A 11/1993 Forse et al.
5,516,801 A * 5/1996 Horrobin ............... 514/560

FOREIGN PATENT DOCUMENTS

| EP | 0635266 | | 1/1995 |
| EP | 0704211 | | 4/1996 |
| JP | 7-41421 | * | 2/1995 |
| WO | 96/36330 | | 11/1996 |

OTHER PUBLICATIONS

Larry E. Boh, MS. RPH, Osteoarthritis, Ch. 61, Pharmocotherapy, A Pathophysiologic Approach, Elsevier Publishing, p.899–911, 1988.*

Walter O. Lundberg, Ph.D., "The Significance of cis, cis, cis 5, 8, 11 Eicosatrienoic Acid in Essential Fatty Acid Deficiency," Nutrition Reviews, vol. 38, No. 7, 1980, pp. 233–235.

* cited by examiner

Primary Examiner—Russell Travers
(74) Attorney, Agent, or Firm—Burns, Doane, Swecker & Mathis, LLP

(57) ABSTRACT

Drug or foods and drink for prevention or treatment of diseases caused by abnormalities in cartilage tissues in which said drugs or foods and drinks have omega-9 unsaturated fatty acid as an active ingredient.

24 Claims, 3 Drawing Sheets

DRUGS FOR PREVENTION AND TREATMENT OF DISEASES CAUSED BY ABNORMALITIES IN CARTILAGE TISSUES

This application is a 371 of PCT/JP96/02231 filed Aug. 2, 1996 claiming Patent from Japanese Patent Application No. 7-207050 filed Aug. 7, 1995.

TECHNICAL FIELD

The present invention relates to drugs for prevention or treatment of diseases caused by abnormalities in cartilage tissues, containing an omega-9 unsaturated fatty acid as an active ingredient, and foods and drinks having the effect of preventing or alleviating medical conditions caused by abnormalities in cartilage tissues, and to a process for producing said drugs. More specifically, the present invention relates to drugs for prevention or treatment of diseases associated with cartilage degeneration such as arthropathy, osteoarthritis, gonarthrosis, periarthritis scapulo-humeralis, spondylitis deformans, etc. and foods or drinks having the effect of preventing or alleviating joint pains, cinealgia, limited range of motion of joints, swelling joints or hydrarthrosis, etc. containing as an active ingredient at least one compound selected from the group consisting of 6,9-octadecadienoic acid, 8,11-eicosadienoic acid, and 5,8,11-eicosatrienoic acid, and to a process for producing them.

BACKGROUND ART

Arthropathy has been divided into the secondary arthropathy that occurs as a sequela to some underlying disease that causes cartilage degeneration, and the primary arthropathy having no specific underlying diseases. Arthropathy is seen most frequently in the knee joints, and less frequently in the joints of elbow, hip, legs, and fingers. A change to a morbid state causes mainly degeneration of cartilage and the repairing mechanism thereof. The progress of the morbid state leads to changes in synovial membrane, destruction of subchondral bones, cartilage hypertrophy in the joint margins, or neogenesis of bone.

Osteoarthritis is a disease in which chronic degenerative changes and proliferative changes take place simultaneously in joints leading to changes in morphology of joints, and is roughly classified into the primary osteoarthritis and the secondary osteoarthritis. The former is more frequently seen in and after middle ages, wherein aging processes combined with mechanical stress lead to its onset, and the latter is seen in the young generation as well, with its onset being secondary to some evident etiology such as joint trauma, morphological abnormalities, diseases, metabolic disorders, etc. Histologically it is characterized by cartilage abrasion as a result of biochemical changes of cartilage, with cleavage as well as reduced viscoelasticity of cartilage reaching the deep part. Spondylosis deformans is a degenerative lesion of the spine. Although its main cause is age change, involvement of constitutional disposition, environmental factors such as occupation, trauma in a broader sense, etc. has been implicated (cited from "Medical Dictionary, published on Mar. 25, 1991, Nannzanndo").

Especially, with regard to the primary osteoarthritis, the increasing number of patients due to underlying causes of aging of the population has become a major social problem. As a medicinal treatment of osteoarthritis, administration of nonsteroidal anti-inflammatory drugs, intra articular injection of steroids, etc. have been employed in order to prevent inflammation of articular cartilage and periosteum, but these are all symptomatic treatments and, therefore, have not been very successful at present for arresting the progress of cartilage destruction.

As a protection against extraneous cartilage destruction due to mechanical stress etc., a high-molecular hyaluronic acid preparation has been used, but it cannot be considered an essential method of treatment. Ameliorating drugs of endogeneous cartilage destruction due to metabolic disorders of chondrocytes themselves which are becoming evident in the recent progress of biochemical research on chondrocytes, and drugs for causative treatment such as would regenerate cartilage loss or destruction often occurring in osteoarthritis have not been known, and its development has been strongly desired.

DISCLOSURE OF THE INVENTION

Thus, it is an object of the invention to provide drugs that are useful for prevention or treatment of diseases caused by abnormalities in cartilage tissues, in particular, for prevention of disease associated with cartilage degeneration such as, in particular, arthropathy, osteoarthritis, periarthritis scapulo-humeralis, spondylitis deformans, etc. and that have relatively small side effects, and thus are applicable to chronic disorders, and new foods and drinks having the effect of preventing or alleviating medical conditions caused by abnormalities in cartilage tissues.

Cartilage tissues are avascular, which is extremely uncommon as a tissue derived from a mesenchyma, and even normal cartilage tissues contain lipids (Ann. Rheum. Dis., 24, 123–135, 1965). However, excessive accumulation of lipids may be observed as pathomorphism in lipo-hem arthropathy (J. Bone Joint Surg. [Am] 52, 1147–1158, 1970) and precocious arthropathy (Arthritis Rheum. 24, 965–968, 1981). In addition, correlation of abnormal metabolism of lipids with medical conditions has been reported in osteoarthritis as well (Metabolism, 40, 571–576, 1991).

An appropriate amount of lipids and appropriate composition of fatty acids are considered to be important for maintenance of normal metabolism and functions of chondrocytes based on the reports that administration of lipids into a joint of rabbit can induce experimental osteoarthritis-like arthropathy (J. Anat, 133, 309–314, 1981), and can reduce chondral incorporation of $^{35}SO_4$ in essential fatty acids-deficient Wistar rats (Arthritis Rheum., 14, 379, 1971), and that lipid supply is needed for normal growth of chondrocytes (Exp. Cell. Res., 145, 415–423, 1983).

However, the role of the above changes in lipids in initiation and aggravation processes of arthropathy has not been fully studied, and furthermore it is not clear whether the administration of lipids is effective for treatment of arthropathy, especially, osteoarthritis. On the other hand, omega-9 unsaturated fatty acids are known to be localized in cartilage tissues and its contents decrease with aging (FASEB J., 5,344–353, 1991), and believed to be important for maintenance of functions of chondrocytes. Furthermore, 5,8,11-eicosatrienoic acid has been confirmed to have an anti-inflammatory effect on the rat models of carrageenan-induced edema, but its pharmaceutical actions in arthropathy is little known.

Thus, in order to resolve the above problems, the inventors have carried out studies on various unsaturated fatty acids and consequently found that 5,8,11-eicosatrienoic acid has an action of inhibiting cartilage degeneration and that hence it is very useful for prevention or treatment of diseases caused by abnormalities in cartilage tissues, and we have completed the present invention.

MODE FOR CARRYING OUT THE INVENTION

Omega-9 unsaturated fatty acid, an active ingredient of the present invention, is 5,8,11-eicosatrienoic acid, and 6,9-octadecadienoic acid or 8,11-eicosadienoic acid which can be readily converted to 5,8,11-eicosatrienoic acid thereby showing the effect of 5,8,11-eicosatrienoic acid may be employed. They may be used alone or in combination.

The fatty acids of the present invention may be any of the geometric isomers, the cis-form or the trans-form. But since most of the naturally occurring omega-9 unsaturated fatty acids are in the cis-form, the omega-9 unsaturated fatty acids are preferably in the cis-form when used in foods and drinks of the present invention.

Omega-9 unsaturated fatty acids according to the present invention may be employed in the form of free fatty acids, and also in various forms, for example, pharmaceutically acceptable salts such as sodium salts, potassium salts, lithium salts, or other alkali metal salts, salts of other metals such as zinc salts, calcium salts, magnesium salts, mono-, di-, tri-glycerides, esters of lower alcohols, phospholipids, glycolipids, amides, etc. Especially ethyl esters or triglycerides are preferred. The term "lower alcohol" as used herein means monohydric alcohols having not more than six carbon atoms, such as methanol, ethanol, propanol, isopropanol, butanol, pentanol, hexanol, etc. These may be used alone or in combination.

Sources of omega-9 unsaturated fatty acids used in the present invention may be any source. Thus, they may be those produced by microorganisms capable of producing omega-9 unsaturated fatty acids, animal tissues deficiency of essential fatty acids, and cultured cell of animal deficiency of essential fatty acids, chemically or enzymatically synthesized products, or products extracted, isolated, or purified from natural products for example animal cartilages.

Specific examples of microorganisms capable of producing omega-9 unsaturated fatty acids refer to those microorganisms having the enzymatic activity of $\Delta5$ desaturation and the enzymatic activity of $\Delta6$ desaturation, and having reduced or no enzymatic activity of $\Delta12$ desaturation as set forth in Japanese Unexamined Patent Publication No. 5(1993)-91888. For example, Mortierella alpina SAM1861 (FERM BP-3590) may be used.

Free Omega-9 unsaturated fatty acids and their esters may be extracted, isolated, and purified from the above-mentioned omega-9 unsaturated fatty acids-containing products according to the conventional method. When they are obtained from microorganisms, for example, fats and oils obtained from a cultured cell mass by extraction with an organic solvent such as n-hexane, or supercritical gas extraction with carbon dioxide are subjected to hydrolysis or esterification to prepare a free fatty acid mixture or a fatty acid ester mixture, which is then subjected to urea fractionation, liquid-liquid partition chromatography, column chromatography, etc. to obtain the desired free fatty acids or esters of 6,9-octadecadienoic acid, 8,11-eicosadienoic acid, and 5,8,11-eicosatrienoic acid, etc. at a yield of 80% or higher. More particularly, the extraction, isolation, and purification may be carried out in accordance with the methods as set forth in Japanese Unexamined Patent Publication No. 5(1993)-91888.

The omega-9 unsaturated fatty acids, active ingredient of the present invention, need not be highly purified products, but fats and oils containing omega-9 unsaturated fatty acids (said fats and oils may contain triglycerides, diglycerides, monoglycerides, phospholipids, or glycolipids having omega-9 unsaturated fatty acids, or free omega-9 unsaturated fatty acids or their esters), free fatty acids mixtures containing omega-9 unsaturated fatty acids or fatty acid ester mixtures can be used.

Oils and fats containing omega-9 unsaturated fatty acids may be obtained from a cultured cells of microorganism capable of producing omega-9 unsaturated fatty acids by disrupting the cells and by extraction with an organic solvent such as n-hexane, or supercritical gas extraction with carbon dioxide. Alternatively, they may be obtained from a natural product containing omega-9 unsaturated fatty acids by the conventional method. Hydrolysis and esterification of the thus obtained oils and fats can yield a free fatty acid mixture or fatty acid ester mixtures containing omega-9 unsaturated fatty acids. More particularly, the extraction, isolation, and purification from the cultured cells may be carried out in accordance with the method as set forth in Japanese Unexamined Patent Publication No. 5(1993)-91888.

The fatty acids of the present invention may be used orally or parenterally in the field of drugs, quasi-drugs, cosmetics, health-related foods, functional foods, nutritional supplementary foods, foods for the elderly, and foods and drinks.

Diseases caused by abnormalities in cartilage tissues, the subject of the present invention, include, for example, arthropathy of the joints of knees, elbows, hip, legs, fingers, shoulders, etc., osteoarthritis, gonarthrosis, periarthritis scapulo-humeralis, spondylitis deformans, etc. Various medical conditions caused by these diseases are also the subject of the present invention, and include stiffness of joints, cinealgia, limited range of motion of joints, and swelling of joints known as disease conditions of osteoarthritis, pains, especially, cinealgia, limited range of motion, and hydrarthrosis known as disease conditions of gonarthrosis, trachelodynia, back pain, lumbago, irradiating pains of limbs or sometimes the trunk, radiculopathy or myelopathy such as numbness or weakness, high paralysis, bladder and rectal disturbances, intermittent claudication, or cold sensation known as disease conditions of spondylitis deformans. The fatty acids of the present invention have relatively small side effects due to selective inhibition of cartilage degeneration, thus capable of being applied to chronic conditions.

When the active ingredients of the present invention are employed as pharmaceutical drugs, they may be administered in any form conveniently employed for oral or parenteral administration, such as injections (emulsifiable, suspendable, non-aqueous, etc.), or solid injections emulsified or suspended prior to use, transfusion solutions, powders, granules, tablets, capsules, enteric coated tablets, troches, liquid for internal use, suspensions, emulsions, syrups, liquids for external use, fomentations, nasal drops, inhalants, ointments, lotions, suppositories, enteral nutrients, etc. They may be used either alone or in combinations depending on the disease conditions. These may be prepared according to the conventional methods by adding to the main drug pharmacologically and pharmaceutically acceptable adjuvants for manufacture.

Such adjuvants for manufacture used are suitable components for manufacture selected depending on the route of administration such as preparations for internal use (oral drugs), parenteral preparations (injections), drugs for application to mucosa (buccals, troches, suppositories, etc.), preparations for external use (ointments, patches, etc.), and the like. In the oral drugs and drugs for application to mucosa, for example, components for pharmaceutical manufacture such as excipients (for example, starch, lactose, crystalline cellulose, calcium lactate, magnesium metasilicate aluminate, and anhydrous silicic acid), disintegrators (for example, carboxy methyl cellulose, calcium carboxy methyl cellulose, and sodium alginate), lubricants (for example, magnesium stearate, paraffin sulphate, and talc), binders (for example, dimethyl cellulose, gelatin, and polyvinylpyrrolidone), coating agents (for example, hydroxyethylcellulose), corrigents, coloring agents, flavoring agents, etc. may be used. In the injections, components for pharmaceutical manufacture such as solubilizing agents and solution adjuvants (for example, distilled water for injection, physiological saline, propylene glycol, and glycerin), capable of forming aqueous injections, suspending agents (for example, surfactants such as polysorbate 80, tween 80, etc., and gum arabic solution), pH-adjusting agents (for example, organic acids or their metal salts), stabilizers, etc. may be used. In addition, in the drugs for external use components for pharmaceutical manufacture such as aqueous or non-aqueous solubilizing agents or solution adjuvants (for example, alcohols, and fatty acid esters), adhesives (for example, carboxy vinyl polymers, and polysaccharides), emulsifying agents (for example, surfactants), and the like may be used. Since the fatty acids of the present invention are unsaturated fatty acids, it is preferred that they contain anti-oxidants such as butyrated hydroxy toluene, butyrated hydroxy anisole, propyl gallate, pharmaceutically acceptable quinones, α-tocopherols, etc. Especially for treatment of arthropathy, osteoarthritis, gonarthrosis, periarthritis scapulo-humeralis, etc., an active ingredient of the present invention may be suspended in an aqueous solvent, its pH is adjusted to be 6.0 to 7.0 and its osmotic pressure ratio vs. 0.9% physiological saline is adjusted to 0.8 to 1.2 to prepare a dosage form for articular cavity administration. As the above aqueous solvent, for example, physiological saline, a 3 to 5% glucose solution, a 3 to 5% xylitol solution, phosphate buffer, etc. may be used.

As a solubilizing agent for preparing injections, for example, nonionic surfactants for pharmaceutical use, etc. may be used. More specifically, it may be prepared by completely mixing an active ingredient of the present invention with half volume of a nonionic surfactant such as POE (60) hydrogenated castor oil or POE sorbitan monooleate, etc. and then by diluting with physiological saline. As needed, isotonicity, oxidation inhibitor (sodium sulfite, sodium bisulfite, etc.), preservatives (benzoic acids, salicylic acid, etc.), soothing agents, etc. may be optionally added.

In the drugs for prevention or treatment of the present invention, active ingredients of the present invention may be blended with drugs such as hyaluronic acid etc. traditionally used for treatment of diseases caused by abnormalities in cartilage tissues, adrenocorticotropic hormone drugs, local anesthetics, antibiotics, etc. may be added.

Though the dose of the active ingredient of the present invention may vary depending on the purpose of administration and the status (sex, age, weight, etc.) of the patient to be administered, the total amount of the omega-9 unsaturated fatty acids of the present invention, when orally administered to an adult, is in the range of 1 to 5,000 mg per day, preferably 1 to 2,000 mg per day, and more preferably 1 to 1,000 mg per day, and when administered parenterally it is in the range of 0.1 to 500 mg per day, preferably 0.1 to 200 mg per day, and more preferably 0.1 to 100 mg per day. The dose may be controlled as appropriate within the above-mentioned range.

For treatment of arthropathy, osteoarthritis, gonarthrosis, periarthritis scapulo-humeralis, in particular, it is injected into articular cavity for an adult in amounts in the range of 0.1 to 500 mg per each administration, preferably 0.1 to 200 mg per each administration, which is administered once every 1 to 7 days. However, in contrast to the commercially available hyaluronic acid preparation of which administration is limited to injection into the articular cavity due to its property as a protecting agent against mechanical stress, the method of administration of the present invention is not limited to injection into the articular cavity but it may be administered in various methods such as oral administration, enteral nutrients, percutaneous absorption, etc., because the fatty acids of the present invention has the activity of inhibiting degeneration of cartilage tissues.

Fatty acids, active ingredients of the present. invention, are known to be synthesized in the body at deficiency state of essential fatty acids. It is evidently superior in safety because its continuously orally administration in an amount of 2 g/day/kg to 7-week old ICR male mice for two weeks did not cause any abnormal conditions.

When the fatty acids of the present invention are used in foods and drinks, they may be in the form of solid or liquid foods or favorite foods.

The foods containing oils and fats include natural foods containing oils and fats such as meat, fish, nuts, etc., foods to which are added oils and fats on cooking such as chinese foods, ramen noodles, soup, etc., foods for which oils and fats are used as a heating medium such as tenpura (deep-fried fish and vegetables), fried foods, fried beancurd, fried rice, doughnuts, fried dough cake, etc., fat and oil foods or processed foods for which oils and fats are added during processing such as butter, margarine, mayonnaise, dressing, chocolate, instant ramen noodles, caramel, biscuits, cookies, cake, ice cream, etc., foods on which oils and fats are sprayed or applied at the finish of processing such as okaki (rice crackers), hard biscuits, anpan (bean-jam buns), etc., but they are not limited to the above, and include, for example, agricultural products such as bread, noodles, rice, confectionery (candy, chewing gum, goumis, tablet candies, and Japanese cake), bean curd and other processed foods thereof etc., fermentation products such as refined sake, medicinal drinks, mirin (sweet sake), cooking vinegar, soy sauce, miso (fermented soy bean paste), etc., dairy products such as yogurt, ham, beacon, sausage, etc., processed marine products such as kamaboko (boiled fish paste), ageten (deep-fried patty of fish paste), hanpen (light, puffy cake made of ground fish), etc., beverages such as fruit juice drinks, soft drinks, sports drinks, alcohol beverages, tea, etc.

Foods and drinks of the present invention are prepared by mixing a given amount of at least one omega-9 unsaturated fatty acid selected from the group consisting of 6,9-octadecadienoic acid, 8,11-eicosadienoic acid, and 5,8,11-eicosatrienoic acid, or extracts containing one of them as a main ingredient, with a source for food and drink containing substantially no omega-9 unsaturated fatty acids, and then by processing it according to the conventional method of manufacture. The amount mixed may vary depending on the forms and property of the food and it is generally 0.001% by weight or more of the total amount of the food, preferably 0.1% by weight or more, and more preferably 1% by weight or more, but is not limited to the above.

The sources for food and drink containing substantially no omega-9 unsaturated fatty acids according to the present invention include those in which the total amount of 6,9-octadecadienoic acid, 8,11-eicosadienoic acid, and 5,8,11-eicosatrienoic acid is less than one mg, and preferably less than two mg, due to the small amount of omega-9 unsaturated fatty acids contained, or those in which the content of 5,8,11-eicosatrienoic acid is less than one mg, and preferably less than two mg as a daily dose of the final product to which the source for food or drink has been added.

In accordance with the present invention, the extracts containing an omega-9 unsaturated fatty acid as a main ingredient include the fats and oils (said fats and pils may contain triglycerides, diglycerides, monoglycerides, phospholipids, and glycolipids having omega-9 unsaturated fatty acids, or free omega-9 unsaturated fatty acids or their esters, etc.) containing omega-9 unsaturated fatty acids obtained from the cultured cells of a microorganism capable of producing omega-9 unsaturated fatty acids by disrupting the cells through extraction with an organic solvent such as n-hexane or through supercritical gas extraction with carbon dioxide, or by extraction from the natural products containing omega-9 unsaturated fatty acids by the conventional methods, mixtures of free fatty acids or mixtures of fatty acid esters containing omega-9 unsaturated fatty acids. The content of the omega-9 unsaturated fatty acids in said extracts is 1% or higher, preferably 5% or higher, and more preferably 10% or higher, and in particular, the content of 5,8,11-eicosatrienoic acids is 1% or higher, preferably 5% or higher, and more preferably 10% or higher.

When used as health-related foods, functional foods, nutritional supplementary foods, and foods for the elderly, their forms may be the above pharmaceutical drug form, or, for example, the processing forms such as natural liquid diets, semi-digested nutritious foods, and chemical defined diets incorporating, in addition to the present fatty acids, for example, proteins (as the protein source, highly nutritious milk protein having balanced amino acid compositions, bean protein, and egg albumin protein are most widely used, but the digests thereof, oligopeptides of egg whites, hydrolyzates of beans, etc. and single amino acids may be used), saccharides, fats, trace metals, vitamins, emulsifying agents, flavors, etc., health-related drinks, capsules, enteral nutrients, etc., but the form of the above foods and drinks are also acceptable.

The health-related foods, functional foods, nutritional supplementary foods, and foods for the elderly can be produced in the form of powders, granules, tablets, capsules, troches, liquid for internal use, suspensions, emulsions, syrups, health-related drinks, natural liquid diets, semi-digested nutritious diets, chemical defined diets, enteral nutrients, etc. using omega-9 unsaturated fatty acids and/or the extract containing omega-9 unsaturated fatty acids as a main ingredient. More specifically, they may be produced in the form of powders, granules, tablets, capsules, troches, liquid for internal use, suspensions, emulsions, syrups, health-related drinks, natural liquid diets, semi-digested nutritious diets, chemical defined diets, enteral nutrients, etc., using oil or fat containing at least 1%, preferably at least 5%, more preferably at least 10% of omega-9-9 unsaturated fatty acids. At this time, any of the elemental diets or any of functional ingredients may be mixed with oils and fats containing omega-9 unsaturated fatty acid of the present invention.

Furthermore, under the supervision of a nutrican based on directions by the physician, the meal prepared on site by adding the fatty acids of the present invention to any foods at the time of cooking of hospital diets can be given to patients with medical conditions caused by abnormalities in cartilage tissues.

The medical conditions according to the present invention caused by abnormalities in cartilage tissues include various medical conditions caused by diseases such as arthropathy of the joints of knees, elbows, hip, legs, fingers, shoulders etc. osteoarthritis, gonarthrosis, periarthritis scapulohumeralis, spondylitis deformans, etc., and more specifically the medical conditions including stiffness of joints, cinealgia, limited range of motion of joints, and swelling of joints known as disease conditions of osteoarthritis, pains, especially, cinealgia, limited range of motion, and hydrarthrosis known as disease conditions of gonarthrosis, trachelodynia, back pain, lumbago, irradiating pains of limbs or sometimes the trunk, radiculopathy or myelopathy such as numbness or weakness, high paralysis, bladder and rectal disturbances, intermittent claudication, or cold sensation known as disease conditions of spondylitis deformans.

The foods and drinks containing the fatty acids of the present invention are preferably administered orally, for the purpose of preventing or alleviating medical conditions caused by abnormalities in cartilage tissues and maintaining health, in amounts of 1 to 5,000 mg per day of the total amount of the omega-9 unsaturated fatty acids of the present invention, preferably 1 to 2,000 mg per day, and more preferably 1 to 1,000 mg per day.

EXAMPLES

The present invention will now be explained more particularly with reference to the following examples.

Example 1

A Method of Preparing 5,8,11-cis-eicosatrienoic Acid Ethyl Ester Using a Microorganism Having the Ability of Producing an Omega-9 Unsaturated Fatty Acid As the microorganism having the ability of producing an omega-9 unsaturated fatty acid, *Mortierella alpina* SAM1861 (FERM BP-3590), as set forth in Japanese Unexamined Patent Publication No. 5(1993)-91888, having the enzymatic activity of $\Delta 5$ desaturation or the enzymatic activity of $\Delta 6$ desaturation and having no enzymatic activity of $\Delta 12$ desaturation was used. The medium (7 tons, pH 6.3) containing 2% glucose, 1% yeast extract, and 0.1% olive oil was fed into a 10-ton tank and was sterilized, and then the aerated shaking culture of *Mortierella alpina* SAM1861 was carried out for 12 days under the condition of a temperature of 24° C. (from day 0 to day 10 of culture) and 20° C. (from day 10 to day 12 of culture), with aeration at 1.0 vvm, and an agitation at 50 rpm. Feeding culture of glucose was carried out so that the total amount of glucose added was 3.49%. After the culture, granulating drying was conducted to obtain 6.8 kg of the dried cells of the microorganism containing 32.7% of the oils and fats containing omega-9 unsaturated fatty acids. The oils and fats contained in the dried mass obtained were extracted with hexane, purified in the conventional method to obtain 20 kg of oils and fats containing omega-9 unsaturated fatty acids (13.2% of 6,9-cis-octadecadienoic acid, 3.5% of 8,11-cis-eicosadienoic acid, and 11.2% of 5,8,11-cis-eicosatrienoic acid). And then the oils and fats obtained were subjected to esterification, vacuum distillation, and high performance liquid chromatography purification to obtain 260 g of 5,8,11-cis-eicosatrienoic acid ethyl ester (90.1% of 5,8,11-cis-eicosatrienoic acid, 7.9% of 6,9-cis-octadecadienoic acid, 1.4% of oleic acid, and 0.6% of arachidic acid).

Example 2

Models of osteoarthritis were prepared using arthrodesis by cast. The animals used were 12-week old male rabbits (Kbl: NZW, Kitayama Labesu K. K.). Under anesthesia by intramuscular administration of 2 mg/kg of xylazine hydrochloride (Selactal, Bayer A. G.) and 50 mg/kg of ketamine hydrochloride (Ketalar 50 for animals, Sankyo K.K.) (hereinafter referred to as "under anesthesia"), hair was cut off the right hind leg. Then after the region from the upper thigh to the toe was covered with the stockinette and cast pad (3M Medicine K.K.), the knee joint was fixed for three weeks at a stretched and bent position by casting tape (3M Medicine K.K.).

The animals that did not show any abnormality at the completion of arthrodesis by cast were selected and divided into four groups consisting of 4 to 5 animals per group by weight and range of motion of joints so that the average weight and the range of motion of joints of each group became uniform.

Samples administered were prepared by completely mixing 90% of 5,8,11-cis-eicosatrienoic acid ethyl ester (hereinafter referred to as "mead acid") obtained in Example 1 and 62.5 µl of HCO-60 (POE(60) hydrogenated castor oil, Nikko Chemical K.K.), which was then suspended in 100 ml of physiological saline to prepare a 1 mg/ml solution of mead acid. Separately 62.5 µl of HCO-60 was dissolved in 100 ml of physiological saline and was used for preparation of low-dose samples and for the solvent administration group.

The administration groups were established as follows: (1) solvent administration group: 0.6 ml/joint, (2) mead acid low-dose administration group: 0.12 mg mead acid/joint, (3) mead acid high-dose administration group: 0.60 mg mead acid/joint, (4) Artz (registered trade mark) (Seikagaku Kogyo K.K.): 0.6 ml (contains 6 mg of high-molecular sodium hyaluronate)/joint. After cutting hair off the administration site under anesthesia and disinfecting the site with 2% Isodine (Isodine for animals, Meiji Seika K.K.) and 70% ethanol, administration was carried out using a disposable syringe (injection needle: 25 G). Dosage samples were administered in the cavity of right knee joint twice per week for five weeks. As an evaluation of pharmaceutical efficacy, determination of the range of motion was made once a week by applying a load of about 400 g at right angle to the tibial axis and measuring an angle formed against the femoral bone. The difference (maximum stretching angle)—(maximum bending angle) was made the range of motion (ROM) of the right knee joint.

During the experiment, the animals were given free access to the solid feed RC4 (Oriental Kobo K.K.) and public tap water as the drinking water.

After the experiment is over, the pathological examination of the joint was carried out. Thus, under anesthesia with administration of sodium pentobarbital solution (Nembutal injection, Dainabott K.K.) into the auricular vein, observation of the outer surface of the knee joint and ROM measurement were carried out and then the animals were bled to death. After the both hind legs of all the animals were removed, their cavity of right knee joint were visually observed and photographed. For all the animals the femoral bone, tibia epiphysial, and synovial membrane were collected, fixed in 10% neutral buffered formalin solution and then demineralization with EDTA was carried out. After embedding and slicing, the section was subjected to hematoxylin-eosin (H-E) stain and safranine O stain and then observed under microscope.

Figure 1:
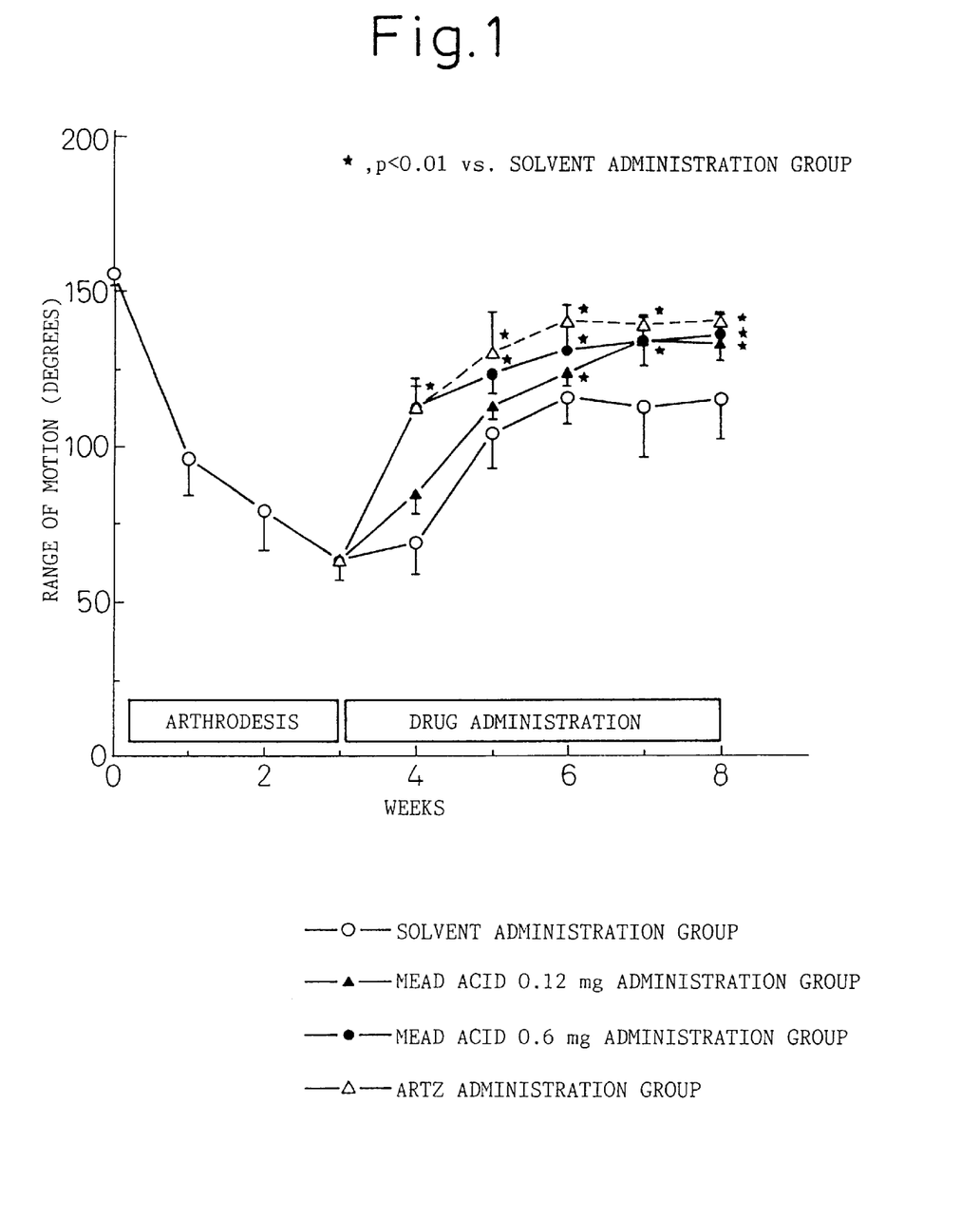
FIG. 1 is a graph showing a therapeutic effect of mead acid on a rabbit model of osteoarthritis.
Figure 2:
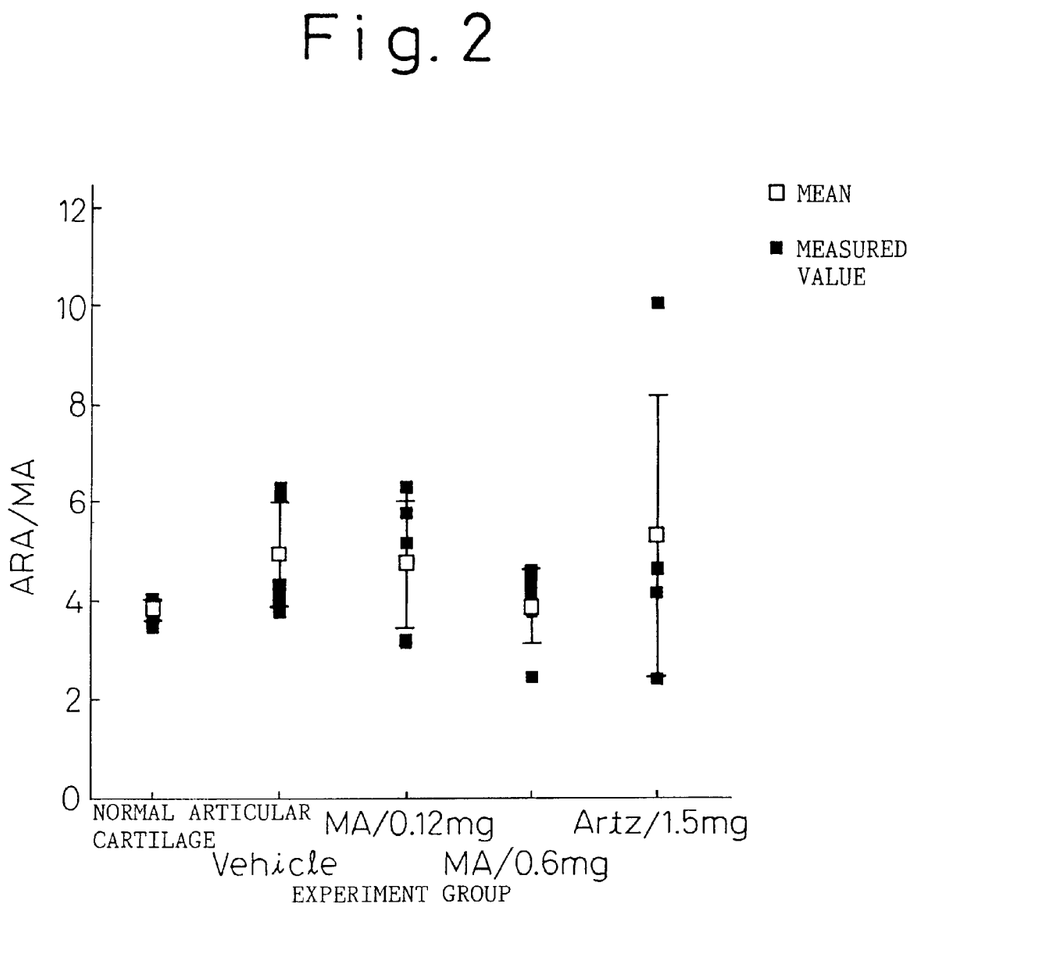
FIG. 2 is a graph showing a mead acid/arachidonic acid ratio in the articular cartilage tissue of a rabbit model of osteoarthritis.

ROM of the joint of the right knee is shown in FIG. 1. One week after the start of administration, mead acid high-dose group and the Artz (registered trade mark) administration group have displayed significant increase in ROM, and by week five it returned to 87% of the pre-constraint value. In the low-dose mead acid group the tendency toward recovery was observed from week two after administration. Results of analysis of fatty acid composition of cartilage tissue at the time of completion of administration are shown in FIG. 2. As compared with the arachidonic acid/mead acid ratio (ARA/MA) of articular cartilage tissue of the untreated rabbits, it became apparent the solvent administration group tended to show elevated values, and the mead acid administration group to return to normal.

Example 3

After 125 µl of 95% 6,9-cis-octadecadienoic acid ethyl ester or 125 µl of 95% 8,11-cis-eicosadienoic acid ethyl ester prepared in the same manner as in Example 1 were completely mixed with 62.5 µl of HCO-60 (POE(60) castor oil, Nikko Chemical K.K.), 1 mg/ml solution of 6,9-cis-octadecadienoic acid ethyl ester (solution A) or 1 mg/ml solution of 8,11-cis-eicosadienoic acid ethyl ester (solution B) suspended 100 ml of physiological saline were prepared. Separately 62.5 µl of HCO-60 was dissolved in 100 ml of physiological saline and was used as the solvent administration group.

In accordance with Example 2, models of osteoarthritis of the knee were prepared using arthrodesis by cast and were divided into three groups of five animals per group so that the average weight and the range of motion of joints of each group became uniform. The administration groups were established as follows: (1) solvent administration group: 0.6 ml/joint, (2) 6,9-cis-octadecadienoic acid ethyl ester administration group: 0.6 ml solution A/joint, (3) 8,11-cis-eicosadienoic acid ethyl ester administration group: 0.60 ml solution B/joint. In accordance with Example 2, dosage samples were administered in the right articular cavity twice per week for five weeks and ROM of the joint of the right knee was measured.

As a result, ROM at week five after the start of administration for the solvent administration group, the solution A administration group, and the solution B administration group were 70%, 80.2%, and 83.6%, respectively, showing significant recovery effects.

Example 4

Preparation of Soft Capsules

| | |
|---|---|
| Gelatin | 70.0% |
| Glycerin | 22.9% |
| Methyl paraoxybenzoate | 0.15% |
| Propyl paraoxybenzoate | 0.51% |
| Water | a suitable amount |
| Total | 100% |

Into the soft capsule coating comprising the above ingredients, 5,8,11-cis-eicosatrienoic acid ethyl ester was filled according to the conventional method to obtain soft capsules containing 180 mg per capsule.

Example 5

Preparation of Soft Capsules

The oily substance comprising 0.3% by weight of a-tocopherol added to 99.7% of omega-9 unsaturated fatty acid-containing triglyceride oil (14.5% by weight of 6,9-cisoctadecadienoic acid, 2.3% by weight of 8,11-cis-eicosadienoic acid, and 17.4% by weight of 5,8,11-cis-eicosatrienoic acid) prepared from the omega-9 unsaturated fatty acid-producing microorganism SAM1861 according to the method as set forth in Japanese Unexamined Patent Publication No. 5(1993)-91888 was filled into the soft capsule coating comprising the ingredients as described in Example 4, according to the conventional method to obtain soft capsules containing 180 mg per capsule.

Example 6

Preparation of Juice

β-cyclodextrinz was dissolved in 20 ml of 20% ethanol solution in water and, while stirring with a stirrer, 100 mg of 5,8,11-cis-eicosatrienoic acid ethyl ester was added thereto followed by incubation at 50° C. for two hours. After cooling at room temperature (about one hour), the mixture was incubated at 4° C. for 10 hours while stirring was continued. The precipitate that formed was recovered by centrifuge, washed with n-hexane, and then lyophilized to obtain 1.8 g of an inclusion compound of 5,8,11-cis-eicosatrienoic acid ethyl ester. One gram of this powder was mixed uniformly with 10 liters of juice to prepare a juice containing 5,8,11-cis-eicosatrienoic acid ethyl ester.

Example 7

Fat Transfusion Solution

Forty grams of 5,8,11-eicosatrienoic acid ethyl ester, 360 g of purified soybean oil, 48 g of purified egg yolk lecithin, 20 g of oleic acid, 100 g of concentrated glycerin and 40 ml of 0.1N caustic soda were added and dispersed by a homogenizer, and then distilled water for injection was added thereto to make 4 liters. This was emulsified by a high-pressure spray-type emulsifier to prepare a lipid emulsion. The lipid emulsion was dispensed in 200 ml aliquots into a plastic bag and then was subjected to high-pressure steam sterilization at 121° C. for 20 min. to prepare a fat transfusion solution.

Example 8

Emulsifiable Injection

Ninety % by weight of 5,8,11-eicosatrienoic acid ethyl ester was prepared as a parenteral emulsion in the following formulation according to the conventional method. The content of mead acid in the parenteral emulsion was 15% (w/v), to which was added 1.2% (w/v) of egg yolk lecithin as the emulsifying agent, and its osmotic pressure was adjusted using glycerin to be isotonic with the blood.

Example 9

Emulsifiable Injection

The omega-9 unsaturated fatty acid-containing triglyceride used in Example 5 was prepared as a parenteral emulsion according to the conventional method. The content of the omega-9 unsaturated fatty acid-containing triglyceride in the parenteral emulsion was 10% (w/v), to which was added 1.2% (w/v) of egg yolk lecithin as the emulsifying agent, and its osmotic pressure was adjusted using glycerin to be isotonic with the blood.

Example 10

Using the primary culture of chondrocytes of the rabbit knee joint, the effects of mead acid on the synthesis of type II collagen was compared with that of other fatty acids, in particular arachidonic acid. The mead acid used was 99% 5,8,11-cis-eicosatrienoic acid ethyl ester highly purified in the same manner as in Example 1, and for arachidonic acid, oleic acid and linoleic acid, the commercially available 99% ethyl esters thereof were used. Chondrocytes were prepared from the knee joints of 4-week old Japan white rabbits in accordance with the method of Suzuki and Shimomura [Shimomurra, Y., Yoneda, T., Suzuki, F. Osteogenesis by chondrocyte from growth cartilage of rat rib., Calcif. Tissue Int., 19:179–187, 1975]. The chondrocytes were plated at 10,000 cells/well of the 96-well plate (Iwaki Glass K.K.) in (MEM medium (50 µg/ml vitamin C, 1 ng/ml b-FGF were added) supplemented with 10% bovine calf serum, and pre-incubated for two days (5% $CO_2$, 37° C.). The fatty acids were suspended in 0.0625% HCO-60 prior to use. As the pre-treatment with the fatty acids, the plates were divided into three groups and added thereto the solvent (0.0625% HCO-60) (group A), mead acid (the final concentration, 300 µM) (group B), and arachidonic acid (the final concentration, 300 µM) (group C), and then incubated for about 5 days while the culture medium and the fatty acids were replaced with fresh ones every two days.

Subsequently, the culture medium was replaced with αMEM medium (1 µg/ml transferrin, 1 µM dexamethasone, 2 µg/ml insulin, 50 µg/ml vitamin C) and each fatty acid (mead acid, arachidonic acid, oleic acid, and linoleic acid) was added thereto to a final concentration of 300 µM followed by incubation for seven days to synthesize extracellular matrix. The culture medium and each of the fatty acids were replaced every 2 days with freshly prepared ones. Pepsin (2 mg/ml) acetate solution was added to the plate at 200 µl/well and treated at 37° C. for 24 hours. The residue was recovered from each well and was centrifuged at 15,000 rpm for 10 minutes to form a precipitate, which was then washed once with tris-EDTA buffer (pH 8.0) and dissolved in 100 µl of the SDS sample buffer.

Figure 3:
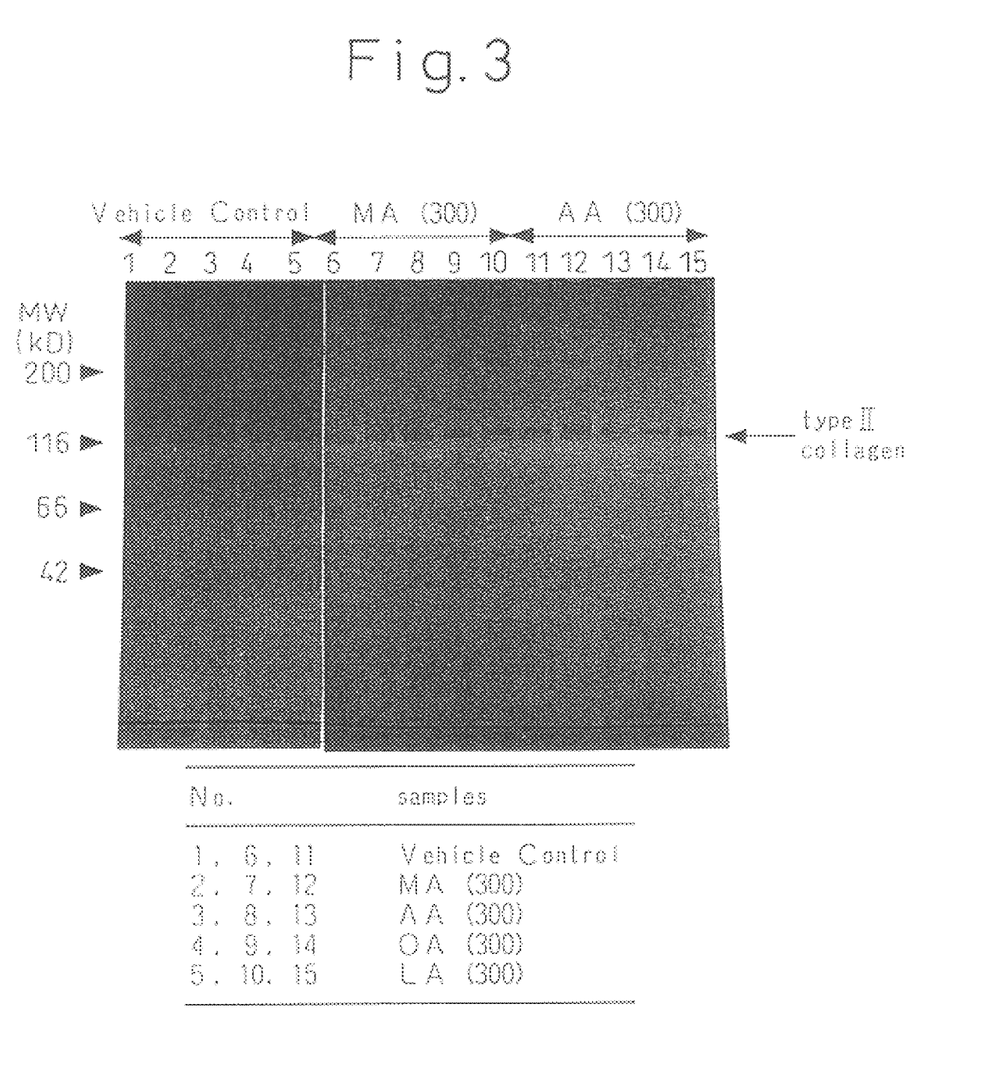
FIG. 3 is an electrophoretic pattern showing the effect of various fatty acids on the synthesis of type II collagen by a chondrocyte

The amount of type II collagen synthesized was determined by electrophoresing 1/10 volume of each sample solution on the multigel 4/20 (Daiichi Kagaku K.K.) and measuring the density of the 116 kD band after staining with Cooumassie Brilliant Blue. The photograph of the stained gel is shown in FIG. 3. It revealed that the addition of arachidonic acid (300 µM) inhibited synthesis of type II collagen (FIG. 3, sample No. 1–5). The inhibition was more conspicuous in result of group C pretreated with arachidonic acid but was recovered by the addition of mead acid (300 µM) (FIG. 3, sample No. 11–15). The activity of recovering the inhibited synthesis of type II collagen by arachidonic acid was unique to mead acid and was not observed in other fatty acids such as oleic acid or linoleic acid. Furthermore, the result of group B pretreated with mead acid (300 µM) indicated that the pretreatment with mead acid inhibited the reduction in synthesis of type II collagen induced by the addition of arachidonic acid (FIG. 3, sample No. 6–10).

What is claimed is:

1. A method for prevention or treatment of gonarthrosis by inhibiting degeneration of cartilage comprising administering to a subject in need of such treatment an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

2. A method for prevention or treatment of gonarthrosis by inhibiting degeneration of cartilage comprising administering to a subject in need of such treatment a food or drink which comprises an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

3. A method for prevention or treatment of spondylitis deformans by inhibiting degeneration of cartilage comprising administering to a subject in need of such treatment an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

4. A method for prevention or treatment of spondylitis deformans by inhibiting degeneration of cartilage comprising administering to a subject in need of such treatment a food or drink which comprises an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

5. A method for prevention or treatment of osteoarthritis by inhibiting degeneration of cartilage comprising administering to a subject in need of such treatment an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

6. A method for prevention or treatment of osteoarthritis by inhibiting degeneration of cartilage comprising administering to a subject in need of such treatment a food or drink which comprises an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

7. A method according to claim 6, wherein the food or drink is a functional food.

8. A method according to claim 6, wherein the food or drink is a nutritional supplementary food.

9. A method according to claim 6, wherein the food or drink is a food for the elderly.

10. A method according to claim 6, wherein the food or drink is in a form selected from the group consisting of powders, granules, tablets, capsules, troches, liquid for intestinal use, suspension, emulsion, syrup, health-related drinks and enteral nutrients.

11. A method for prevention or treatment of osteoarthritis selected from the group consisting of hip osteoarthritis, leg osteoarthritis, finger osteoarthritis and shoulder osteoarthritis by inhibiting degeneration of cartilage comprising administering to a subject in need of such treatment an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

12. A method for prevention or treatment of osteoarthritis selected from the group consisting of hip osteoarthritis, leg osteoarthritis, finger osteoarthritis and shoulder osteoarthritis by inhibiting degeneration of cartilage comprising administering to a subject in need of such treatment a food or drink which comprises an omega-9 unsaturated fatty acid in an amount effective for preventing or treating said disease, wherein the omega-9 unsaturated fatty acid is at least one compound selected from the group consisting of 6,9-octadecadienoic acid, 8,11-eicosadienoic acid and 5,8,11-eicosatrienoic acid.

13. A method according to claim 12, wherein the food or drink is a functional food.

14. A method according to claim 12, wherein the food or drink is a nutritional supplementary food.

15. A method according to claim 12, wherein the food or drink is a food for the elderly.

16. A method according to claim 12, wherein the food or drink is in a form selected from the group consisting of powders, granules, tablets, capsules, troches, liquid for intestinal use, suspension, emulsion, syrup, health-related drinks and enteral nutrients.

17. A method according to claim 2, wherein the food or drink is a functional food.

18. A method according to claim 2, wherein the food or drink is a nutritional supplementary food.

19. A method according to claim 2, wherein the food or drink is a food for the elderly.

20. A method according to claim 2, wherein the food or drink is in a form selected from the group consisting of powders, granules, tablets, capsules, troches, liquid for intestinal use, suspension, emulsion, syrup, health-related drinks and enteral nutrients.

21. A method according to claim 4, wherein the food or drink is a functional food.

22. A method according to claim 4, wherein the food or drink is a nutritional supplementary food.

23. A method according to claim 4, wherein the food or drink is a food for the elderly.

24. A method according to claim 4, wherein the food or drink is in a form selected from the group consisting of powders, granules, tablets, capsules, troches, liquid for intestinal use, suspension, emulsion, syrup, health-related drinks and enteral nutrients.

* * * * *